United States Patent
Podany et al.

(10) Patent No.: US 7,662,099 B2
(45) Date of Patent: Feb. 16, 2010

(54) METHOD AND INSTRUMENTATION TO SENSE THERMAL LESION FORMATION BY ULTRASOUND IMAGING

(75) Inventors: Vaclav O. Podany, New Fairfield, CT (US); Jonathan Kwok, Somerset, NJ (US); Rajesh Pendekanti, Bridgewater, NJ (US)

(73) Assignee: Ethicon, Inc., Somerville, NJ (US)

( * ) Notice: Subject to any disclaimer, the term of this patent is extended or adjusted under 35 U.S.C. 154(b) by 851 days.

(21) Appl. No.: 10/609,696

(22) Filed: Jun. 30, 2003

(65) Prior Publication Data

US 2004/0267120 A1    Dec. 30, 2004

(51) Int. Cl.
*A61B 8/00* (2006.01)

(52) U.S. Cl. ............ 600/439; 600/437; 600/443; 600/446; 600/459

(58) Field of Classification Search ......... 600/437–461; 604/19, 20
See application file for complete search history.

(56) References Cited

U.S. PATENT DOCUMENTS

| | | | | |
|---|---|---|---|---|
| 4,742,829 A * | 5/1988 | Law et al. | .................... | 600/461 |
| 4,932,414 A | 6/1990 | Coleman et al. | | |
| 5,127,393 A * | 7/1992 | McFarlin et al. | ............ | 600/114 |
| 5,325,860 A * | 7/1994 | Seward et al. | ................ | 600/468 |
| 5,391,140 A * | 2/1995 | Schaetzle et al. | ................ | 601/4 |
| 5,435,304 A * | 7/1995 | Oppelt et al. | ................ | 600/439 |
| 5,471,988 A * | 12/1995 | Fujio et al. | .................... | 600/439 |
| 5,526,815 A * | 6/1996 | Granz et al. | ................ | 600/439 |
| 5,558,092 A * | 9/1996 | Unger et al. | ................ | 600/439 |
| 5,657,760 A * | 8/1997 | Ying et al. | .................... | 600/439 |
| 5,803,083 A * | 9/1998 | Buck et al. | .................... | 600/439 |
| 5,853,368 A * | 12/1998 | Solomon et al. | ............ | 600/439 |
| 5,876,344 A * | 3/1999 | Baker et al. | ................. | 600/463 |
| 5,976,092 A * | 11/1999 | Chinn | ......................... | 600/459 |
| 6,216,704 B1 * | 4/2001 | Ingle et al. | .................... | 128/898 |
| 6,241,744 B1 * | 6/2001 | Imran et al. | ................. | 606/159 |
| 6,394,955 B1 | 5/2002 | Perlitz | | |
| 6,425,867 B1 * | 7/2002 | Vaezy et al. | ................ | 600/439 |
| 6,485,413 B1 * | 11/2002 | Boppart et al. | .............. | 600/160 |
| 6,508,774 B1 * | 1/2003 | Acker et al. | .................... | 601/2 |
| 6,517,530 B1 * | 2/2003 | Kleven | .......................... | 606/1 |
| 6,635,017 B1 * | 10/2003 | Moehring et al. | ............ | 600/439 |
| 6,638,286 B1 * | 10/2003 | Burbank et al. | .............. | 606/157 |
| 2003/0028095 A1 * | 2/2003 | Tulley et al. | ................. | 600/422 |
| 2003/0225332 A1 * | 12/2003 | Okada et al. | ................. | 600/439 |

* cited by examiner

*Primary Examiner*—Brian Casler
*Assistant Examiner*—Nasir Shahrestani
(74) *Attorney, Agent, or Firm*—Scully, Scott, Murphy & Presser, P.C.

(57) ABSTRACT

A combination therapy and imaging instrument is provided. The instrument includes: a therapy probe for producing energy to alter tissue; and an imaging probe proximate the therapy probe for imaging the tissue altered with the therapy probe.

22 Claims, 3 Drawing Sheets

METHOD AND INSTRUMENTATION TO SENSE THERMAL LESION FORMATION BY ULTRASOUND IMAGING

BACKGROUND OF THE INVENTION

1. Field of the Invention

The present invention relates generally to ultrasonic medical instrumentation, and more particularly, to methods and instrumentation for creating and sensing thermal lesion formation with ultrasound and/or radio frequency energy.

2. Prior Art

Ultrasonic and radio frequency (RF) instruments are well known in the medical arts. Such instrumentation may be used to make lesions in tissue. The operation of most available treatment systems is based on a fixed procedure time, that is the ultrasonic or RF energy is applied to the tissue for a predetermined period of time. Typically, the predetermined period of time is based on the worst-case scenario in order to ensure treatment efficacy. Under this method, tissue may be over ablated and peripheral thermal damage is prevalent and undesirable.

There are systems known in the art that measure the electrical impedance of the tissue to determine the efficacy of the lesion created. However, such a method has been found to be applicable only for select treatment modalities. Still other systems utilize a functional testing of the lesion (e.g., pacing and sensing across the lesion). However, such methods have been found to misrepresent how efficacious the lesion is. For instance, the functional signal may be blocked by something other than the lesion.

SUMMARY OF THE INVENTION

Therefore it is an object of the present invention to provide methods and instrumentation for creating lesions and determining the efficacy of lesions in tissue that overcome the disadvantages of conventional methods and instrumentation known in the art.

Accordingly, a combination therapy and imaging instrument is provided. The instrument can comprise: a therapy probe for producing energy to alter tissue; and an imaging probe proximate the therapy probe for imaging the tissue altered with the therapy probe. The therapy probe can comprise an ultrasonic transducer operatively connected to an ultrasonic generator, in which case the ultrasonic transducer can alter the tissue by creating a lesion in the tissue. The therapy probe can also comprise one or more radio frequency electrodes operatively connected to a power source, in which case the one or more radio frequency electrodes alters the tissue by creating a lesion in the tissue. The imaging probe can be an ultrasonic imaging transducer.

The combination therapy and imaging instrument can further comprise connection means for removably connecting the therapy probe to the imaging probe. The therapy probe can be disposable and the imaging probe can be reusable. The connection means can comprise a key formed on one of the therapy probe and the imaging probe and a mating keyway formed on the other of the therapy probe and the imaging probe. The therapy probe and imaging probe can be arranged side by side along a surface of the tissue.

Also provided is an instrument comprising: a therapy probe for producing energy to alter tissue; an imaging probe proximate the therapy probe for imaging the tissue altered with the therapy probe; and connection means for connecting the therapy probe to the imaging probe.

Still also provided is a combination therapy and imaging instrument comprising: therapy means for producing energy to alter tissue; imaging means for imaging the tissue altered with the therapy probe; and connecting means for connecting the therapy and imaging means together.

Still further provided is a method for forming a lesion in tissue and checking the efficacy of the lesion. The method comprising: creating a lesion in the tissue with a therapy probe; and imaging the lesion created with an imaging probe connected to the therapy probe. The method can further comprise determining the efficacy of the lesion created by the therapy probe based on the results of the imaging. The determining can comprise performing normal B-scan ultrasonic imaging of the lesion, or performing ultrasonic Doppler enhanced imaging of the lesion, such as sonoelastic imaging of the lesion.

The creating of the lesion can comprise applying an electrical current through the tissue and/or directing ultrasonic energy to the tissue. The imaging of the lesion can comprise directing an ultrasonic energy through the tissue.

Still further provided is a combination therapy and imaging instrument. The instrument comprising an ultrasound therapy and imaging probe for producing energy to alter tissue and for imaging the altered tissue, the therapy and imaging probes being operatively connected to a common ultrasonic generator Still further provided is an instrument for imaging lesions in tissue, the instrument comprising an imaging probe for imaging the lesion, the imaging probe having connecting means for connection of a separable therapy probe thereon.

Still further provided is a therapy probe for producing energy to alter tissue, the therapy probe having connecting means for connection of a separable imaging probe thereon.

Still yet provided is a method for forming a lesion in tissue, where the method comprises: creating a lesion in the tissue with a therapy probe; imaging the lesion created with an imaging probe connected to the therapy probe; determining the efficacy of the lesion created by the therapy probe based on the results of the imaging; and controlling the creating based on the results of the determining. At least one of the determining and controlling can be automatically performed.

BRIEF DESCRIPTION OF THE DRAWINGS

These and other features, aspects, and advantages of the apparatus and methods of the present invention will become better understood with regard to the following description, appended claims, and accompanying drawings where:

DETAILED DESCRIPTION OF THE PREFERRED EMBODIMENT

Although this invention is applicable to numerous and various types of instrumentation for imaging lesions in tissue, it has been found particularly useful in the environment of ultrasound imaging. Therefore, without limiting the applicability of the invention to ultrasound imaging, the invention will be described in such environment. Furthermore, although this invention is applicable to numerous and various types of therapy modalities for creating lesions in tissue, it has been found particularly useful in the environment of ultrasound and radio-frequency modalities. Therefore, without limiting the applicability of the invention to ultrasound and radio-frequency modalities for creating lesions in tissue, the invention will be described in such environment. Other possible modalities for creating lesions in tissue include microwave, laser, and cryo modalities.

Figure 1:
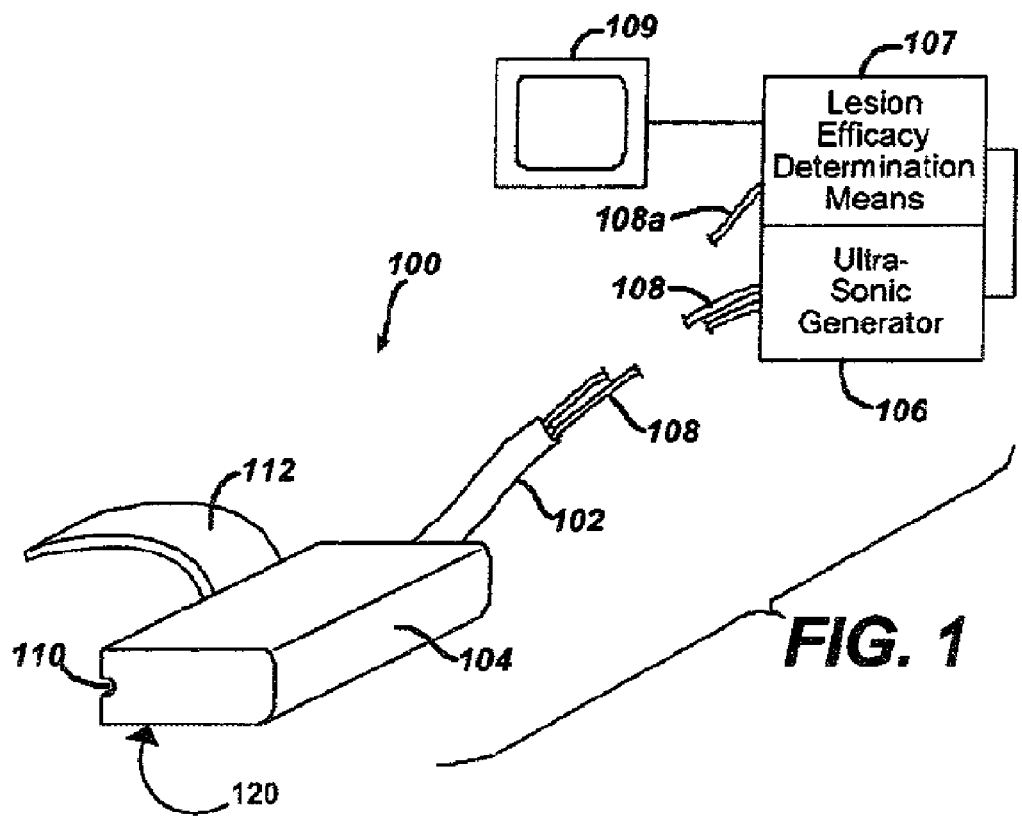
FIG. 1 illustrates a partial isometric view of an ultrasonic imaging probe and system according to an embodiment of the invention.

Referring now to FIG. 1, an imaging probe 100 is shown therein as well as a system for use therewith. The imaging probe 100 is shown having a rigid tubular body 102 by way of example only. Those skilled in the art will appreciate that the imaging probe 100 can be configured in other ways, such as an open surgical instrument, endoscopic instrument, less invasive instrument, or a catheter. Furthermore, the imaging probe 100 can be configured as a finger probe similar to that disclosed in co-pending U.S. patent application Ser. No. 10/609,695, entitled Ultrasonic Finger Probe, the entire contents of which is incorporated herein by its reference. The imaging probe 100 preferably uses ultrasonic energy to image tissue. The imaging probe 100 in such a configuration generally has an ultrasonic transducer (not shown) disposed in a body 104. The ultrasonic energy produced by the ultrasonic transducer is transmitted through an ultrasonic energy transmitting surface 120 of the imaging probe 100 and subsequently applied to the tissue intended to be imaged. The ultrasonic energy transmitting surface 120 is configured to directly contact the surface of the tissue. Ultrasonic transducers for imaging tissue are well known in the art, such as a system which uses phased array ultrasound, and a detailed description thereof is omitted for the sake of brevity. The ultrasonic transducer is operatively coupled to an ultrasonic generator 106 by wiring 108. The wiring 108 can be externally routed or routed in an interior of the tubular body 102 as shown in FIG. 1. The wiring 108 is generally connected to the ultrasonic generator 106 by a switch (not shown) for selectively providing the ultrasonic energy to the imaging transducer. Furthermore, the ultrasonic generator 106 may be remote from the probe 100 or integrally provided therein, such as in a handle portion (not shown) of the probe.

Figure 2:
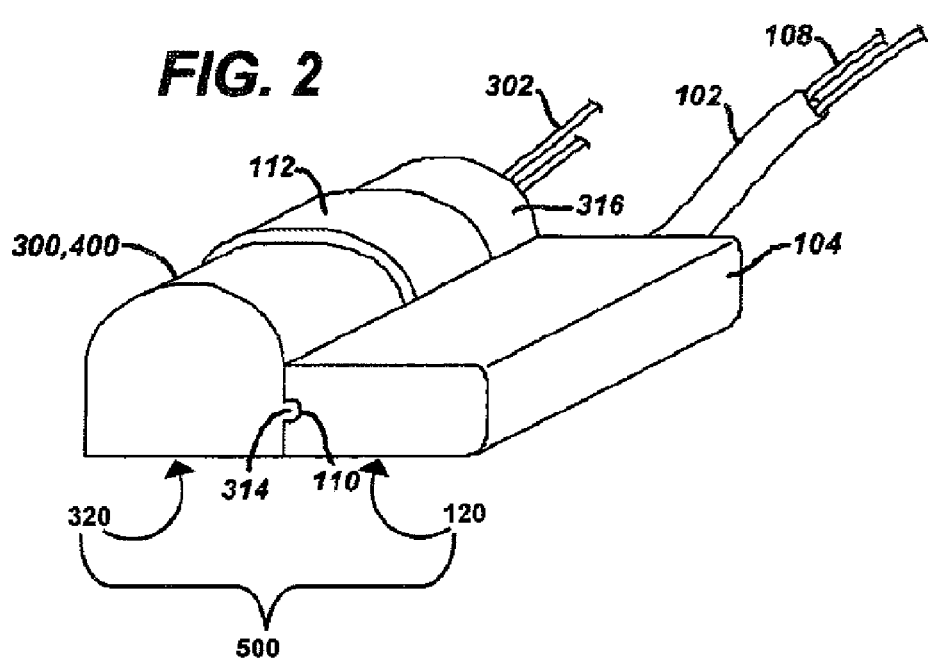
FIG. 2 illustrates a partial isometric view of a therapy probe removably coupled to the ultrasonic imaging probe of FIG. 1.
Figure 3:
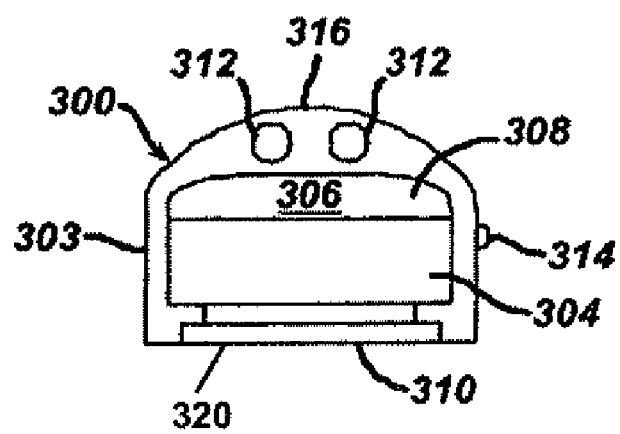
FIG. 3 illustrates a sectional view of the therapy probe of FIG. 2 where the therapy probe is an ultrasonic probe.
Figure 4:
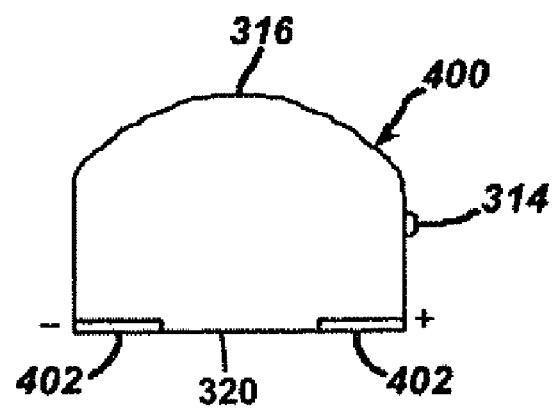
FIG. 4 illustrates a sectional view of the therapy probe of FIG. 2 where the therapy probe is a radio frequency probe.

The probe 100 is preferably used in combination with a therapy probe 200, as shown in FIG. 2, for producing energy to alter tissue, such as creating a lesion in the tissue. In one embodiment, the therapy probe comprises an ultrasonic transducer 300, as shown in FIG. 3, operatively connected to the ultrasonic generator 106. In another embodiment, the therapy probe can comprise a radio-frequency probe 400, as shown in FIG. 4, operatively connected to an electro-surgical unit (not shown). The ultrasonic probe 300 can be operatively connected to the same ultrasonic generator 106 as the imaging probe or use a separate ultrasonic generator dedicated to generating ultrasonic energy and directing the same to the therapy probe 300. Furthermore, the therapy probe 300, 400 can have separable wiring 302 for operatively connecting the same to an ultrasonic generator or electro-surgical unit (also preferably through a switch). Alternatively, the imaging probe 100 can have contacts (not shown) that correspond with mating contacts (not shown) on the therapy probe 300, 400 for connecting to the ultrasonic generator or electro-surgical unit through the imaging probe 100.

Referring now to FIG. 3 in detail, the ultrasonic therapy probe 300 has an ultrasonic transducer 304 housed in a cavity 306 of the body 303. The cavity 306 is preferably oversized to provide an air-backing 308 to increase the efficiency of the ultrasonic transducer 304. The cavity 306 is preferably closed on a surface proximate the tissue to be altered by an acoustic window 310 fabricated from any material that transmits ultrasonic energy. Additionally, the ultrasonic transducer 304 may have an impedance matching coating (not shown) on the side of the ultrasonic transducer 304 that faces the acoustic window 310. Accordingly, an energy transmitting surface 320 of the therapy probe 300 is defined at the lower surface of the acoustic window 310, through which energy produced by the therapy probe 300 is transmitted and subsequently applied to the tissue. The energy transmitting surface 320 is configured to directly contact the surface of the tissue. Furthermore, the body 303 may include one or more conduits 312 for re-circulation or passage of a cooling medium, such as water or saline to cool the ultrasonic transducer 304 to improve the efficiency thereof. These and other features of the ultrasonic transducer 304 are more fully discussed in co-pending U.S. patent application Ser. No. 10/609,692, entitled System For Creating Linear Lesions for the Treatment of Atrial Fibrillation, the entire contents of which are incorporated herein by its reference. Alternatively, the same transducer may be used for both imaging and therapy, however some of the features that provide for efficient therapy, such as the air backing 308 may not be consistent with efficient imaging.

Referring now to FIG. 4, the radio frequency therapy probe 400 can comprise one or more radio frequency electrodes 402 operatively connected to a power source, such as the electro-surgical unit. Preferably, the radio frequency probe 400 is configured as a bipolar instrument having one or more electrodes 402 at a first polarity (e.g., +) and one or more electrodes at a second polarity (e.g., −). However, those skilled in the art will appreciate that the radio frequency probe may also be configured as a monopolar instrument and used with an appropriate grounding plate as is known in the art. The electrodes 402 are fabricated from a conductive material, such as stainless steel and the remaining portions of the body 102 are non-conductive, either by virtue of being fabricated from a non-conductive material such as a polymer or being coated with a non-conductive material such as PTFE. As discussed above with regard to the ultrasound therapy probe 300, the radio frequency probe 400 preferably alters the tissue by creating a lesion therein.

Referring back to FIGS. 3 and 4, the probes 100, 300, 400 can have a connection means for removably connecting the therapy probe 300, 400 to the imaging probe 100. The connection means can comprise a key formed on one of the therapy probe 300, 400 and the imaging probe 100 and a mating keyway formed on the other of the therapy probe 300, 400 and the imaging probe 100. Preferably, the key 314 is provided on the therapy probe 300, 400 and the mating keyway 110 is provided on the imaging probe 100. A clip 112 may also be provided on the imaging probe 100 to provide further support of the therapy probe 300, 400. The clip 112 preferably has a curved shape that mimics a corresponding curved shape of a surface 316 of the body 303 of the therapy probe 300, 400. Preferably, as shown in FIG. 2, the therapy probe 300, 400 and imaging probe 100 are arranged side by side along a surface of the tissue, however, those skilled in the art will appreciate that they may be arranged in other configurations. More preferably, as depicted in FIG. 2, when the key 314 and the mating keyway 110 engage each other to removably connect the therapy probe 300 to the imaging probe 100, the energy transmitting surface 320 of the therapy probe 300 is aligned with the ultrasonic energy transmitting surface 120 of the imaging probe 100, thereby providing a unitary energy transmitting surface 500 configured to be in contact with the surface of the tissue for performing tissue alteration and tissue imaging simultaneously. Those skilled in the art will also appreciate that the connection means also lends itself to providing the therapy probe 300, 400 in a disposable configuration. In such a configuration, the imaging probe may be reusable or may also be disposable.

The use and operation of the imaging 100 and/or therapy probes 300, 400 will now be described with reference to FIG. 2 and FIGS. 5a, 5b, 6a, and 6b. The imaging 100 and therapy probes 300, 400 discussed above have particular utility in forming a lesion in tissue and checking the efficacy of the lesion. Because the efficacy of the lesion created with the therapy probe 300, 400 can be easily checked with the imaging probe, over ablation and peripheral thermal damage of the tissue is prevented.

The method generally comprises coupling the therapy probe 300, 400 to the imaging probe 100 and positioning the therapy probe 300, 400 over the tissue that is to be ablated. The therapy probe 300, 400 is then energized with ultrasound or radio frequency energy from an appropriate source, such as an ultrasonic generator 106 or an electro-surgical unit through operation of a switch. The switch can be integral with the instrument probe 100 or remote therefrom, such as a foot switch (not shown). The lesion created by the therapy probe 300, 400 is then checked to provide an analysis of its formation, including transmurality, continuity, and completeness. The lesion may be imaged continuously during treatment (in real time), intermittently during treatment, or as a comparison between single pre-treatment and post treatment images. The images are preferably viewed by a physician or technician on a display while the procedure is being performed. After checking the efficacy of the lesion with the imaging probe 100, the therapy probe 300, 400 may be energized further over the same lesion if it is determined that the lesion is not satisfactory and the same repeated until satisfactory. The therapy probe 300, 400 may also be used to create other lesions which can also be imaged in the same manner as discussed above. After the procedure is complete, the therapy probe 300, 400 may be uncoupled from the imaging probe 100. As discussed above, the therapy probe is preferably configured as a disposable part and is therefore properly disposed of after the procedure is complete. However, the therapy probe 300, 400 may also be properly sterilized and/or disinfected and reused in later procedures. As also discussed above, the imaging probe 100 is preferably configured as a reusable part that may be properly sterilized and/or disinfected and reused in later procedures. However, the imaging probe 100 may also be configured as a disposable instrument.

Although the imaging probe 100 and therapy probe 300, 400 are shown and described as being separable, those skilled in the art will appreciate that they may be integrally formed and may either be configured as a reusable or disposable instrument. Furthermore, the imaging probe 100 is shown connected to further structure, such as the tubular body 102, and the therapy probe 300, 400 being carried by the imaging probe 100. However, those skilled in art will also appreciate that the therapy probe 300, 400 can be connected to further structure, such as the tubular body, and the imaging probe being carried on the therapy probe 300, 400.

Figure 5A:
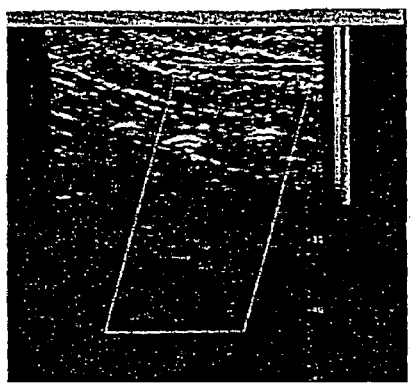
FIGS. 5a and 5b illustrate B-scan images of tissue before and after, respectively, creation of a lesion with a therapy probe.
Figure 5B:
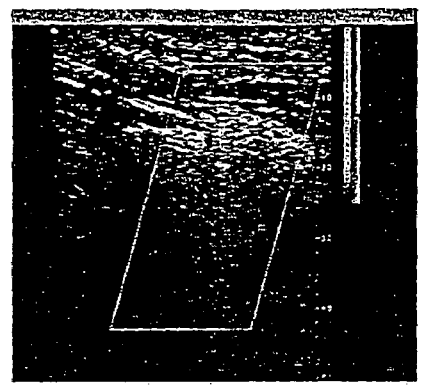
Figure 6A:
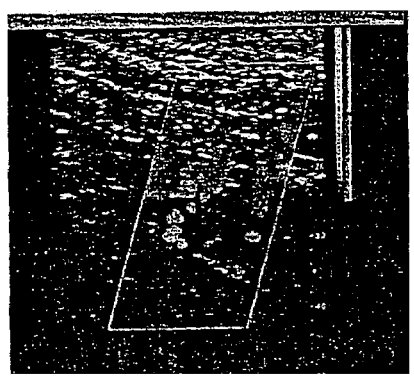
FIGS. 6a and 6b illustrate Doppler images before and after, respectively, creation of a lesion with a therapy probe.
Figure 6B:
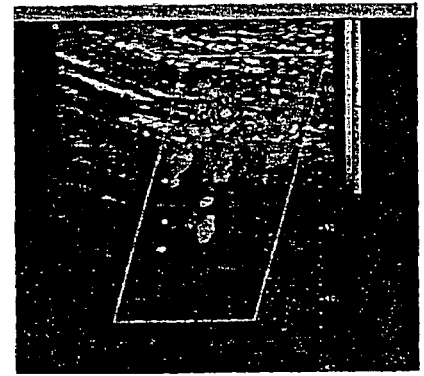

The imaging performed by the imaging probe 100 is preferably ultrasound imaging such as normal B-scan ultrasonic imaging of the lesion or ultrasonic Doppler enhanced imaging of the lesion, such as sonoelastic imaging of the lesion. FIGS. 5a and 5b illustrate visualization of the echogenicity and absorption property changes of tissue before and after creation of a lesion, respectively, using normal B-scan imaging. As can be seen clearly in FIG. 5b, the lesion mass is visible due to a change in acoustic properties in the tissue. Additional properties of the tissue can also be utilized to enhance image contrast. Sonoelastic imaging can be utilized to sense changes in the mechanical properties in the tissue. For example, a displacement can be introduced to the tissue volume containing the lesion by mechanical means or radiation force (e.g., from an ultrasound treatment transducer). The variations in mechanical elasticity due to the lesion will result in different displacements for viable and lesioned tissue. These differences can be visualized using Doppler enhanced ultrasound imaging as shown in FIGS. 6a and 6b. In FIG. 6b, the lesion mass is visible due to the different displacements of the lesioned tissue. Another method of enhancing the image contrast is tissue parameter imaging, which relies on analyzing the spectral characteristics of the returning ultrasound signal for differences arising from tissue type (viable vs. lesioned). A false color scale can be assigned to particular spectral features to provide contrast to the tomographic ultrasound images.

Referring back to FIG. 1, the system shown therein can further comprise a lesion efficacy determination means 107 for determining the efficacy of the lesion created with the therapy probe 300, 400. The lesion efficacy determination means 107 being operatively connected to the imaging probe 104 by way of wiring 108a. The operator could then terminate the therapy when the efficacy has reached 100% or within some nominal predetermined range within 100%. Furthermore, the operator can decide to alter or change the type or level of therapy if the lesion is determined not be very efficacious. The operator preferably views one of the above mentioned imaging techniques on a monitor 109 operatively connected to the lesion efficacy determination means 107 which inputs the data from the imaging probe 104, processes the same according to one of the imaging techniques described above, and outputs the same to the monitor 109 in a format suitable for viewing. The operator is trained to recognize when the lesion is efficacious, possibly by using color-coding to display the lesion in a color different from the color of the untreated surrounding tissue. The lesion efficacy determination means 107 may also provide the user with an indication of the efficacy, based on the input data and an algorithm for determining efficacy.

The indication from the lesion efficacy determination means 107 may also be used to automatically feedback the ultrasonic generator (or other therapy source) (shown as a dashed line) to automatically control the same. For instance, where the lesion efficacy determination means 107 determines that the efficacy of the lesion being created is 100% (or within a predetermined range from 100%) the ultrasonic generator 106 can be powered down such that it no longer supplies ultrasonic energy to the therapy probe 300. Algorithms for analyzing image data, determining or recognizing the status of objects in the image data, and providing feedback control to another component is well known in the art. For instance, an algorithm can be used which distinguishes the ablated tissue from the healthy surrounding tissue, assign a different variable, such as color, to the ablated and healthy tissue, and determine when the color or other variable for the ablated tissue reaches a predetermined criteria. The predetermined criteria will depend upon factors including the type of tissue being ablated, the type of lesion being created, and the therapy modality being used to create the lesion.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. A combination therapy and imaging instrument, the instrument comprising:

a therapy probe for producing energy to alter tissue, the therapy probe comprising a side surface and an energy transmitting surface adapted to be in contact with the surface of the tissue, wherein the energy produced is at least one of ultrasonic energy and an electrical current;

an imaging probe for imaging the tissue altered with the therapy probe using ultrasonic energy, the imaging probe comprising a side surface adapted to appose the side surface of the therapy probe and an ultrasonic energy transmitting surface adapted to be in contact with the surface of the tissue, wherein the imaging probe and the therapy probe are adapted to permit simultaneous energy production and imaging of the tissue during tissue alteration; and connection means including a key formed on one of the side surface of the therapy probe and the side surface of the imaging probe and a mating keyway formed on the other of the side surface of the therapy probe and the side surface of the imaging probe, for releasably connecting the therapy probe to the imaging probe and apposing the side surface of the therapy probe and the side surface of the imaging probe, wherein, when the key and the keyway mate with each other to releasably connect the therapy probe and the imaging probe and appose the side surface of the therapy probe and the side surface of the imaging probe, the energy transmitting surface of the therapy probe and the ultrasonic energy transmitting surface of the imaging probe are aligned with each other to define a continuous unitary energy transmitting surface adapted to be in contact with the surface of the tissue for performing simultaneous tissue alteration and tissue imaging.

2. The combination therapy and imaging instrument of claim 1, wherein the therapy probe comprises an ultrasonic transducer operatively connected to an ultrasonic generator.

3. The combination therapy and imaging instrument of claim 2, wherein the ultrasonic transducer is adapted to alter the tissue by creating a lesion in the tissue.

4. The combination therapy and imaging instrument of claim 1, wherein the therapy probe comprises one or more radio frequency electrodes operatively connected to a power source.

5. The combination therapy and imaging instrument of claim 4, wherein the one or more radio frequency electrodes are adapted to alter the tissue by creating a lesion in the tissue.

6. The combination therapy and imaging instrument of claim 1, wherein the imaging probe is an ultrasonic imaging transducer.

7. The combination therapy and imaging instrument of claim 1, wherein the connection means permits the therapy probe and the imaging probe to be disposable and reusable following a sterilization procedure performed on the therapy probe and the imaging probe.

8. The combination therapy and imaging instrument of claim 1, wherein the therapy probe and imaging probe are adapted to be arranged side by side along a surface of the tissue.

9. A combination therapy and imaging instrument, the instrument comprising:

therapy means for producing energy to alter tissue, the therapy means comprising a side surface and an energy transmitting surface adapted to be in contact with the surface of the tissue, wherein the energy produced is at least one of ultrasonic energy and an electrical current;

imaging means for imaging the tissue altered with the therapy means using ultrasonic energy, the imaging means comprising a side surface adapted to appose the side surface of the therapy probe and an ultrasonic energy transmitting surface adapted to be in contact the surface of the tissue, wherein the imaging means and the therapy means are adapted to permit simultaneous energy production and imaging of the tissue during tissue alteration;

connecting means for removably connecting the therapy and imaging means together and apposing the side surface of the therapy means and the side surface of the imaging means, wherein, when the connecting means releasably connect the therapy probe and the imaging probe and appose the side surface of the therapy means and the side surface of the imaging means, the energy transmitting surface of the therapy means and the ultrasonic energy transmitting surface of the imaging means are aligned with each other to define a unitary energy transmitting surface adapted to be in contact with the surface of the tissue for performing simultaneous tissue alteration and tissue imaging.

10. A method for forming a lesion in tissue and checking the efficacy of the lesion, the method comprising:

releasably connecting a therapy probe comprising a side surface and an energy transmitting surface adapted to be in contact with the surface of the tissue to an imaging probe comprising a side surface and an ultrasonic energy transmitting surface adapted to be in contact with the surface of the tissue;

apposing the side surface of the therapy probe and the side surface of the imaging probe and aligning the energy transmitting surface of the therapy probe and the ultrasonic energy transmitting surface of the imaging probe, to define a continuous unitary energy transmitting surface adapted to be in contact with the surface of the tissue for performing simultaneous tissue alteration and tissue imaging;

creating a lesion in the tissue with energy produced by a therapy probe, wherein the energy produced is at least one of ultrasonic energy and an electrical current; and imaging the lesion created with an imaging probe connected to the therapy probe, wherein the imaging probe and the therapy probe are adapted to permit simultaneous energy production and imaging of the lesion during lesion creation.

11. The method of claim 10, further comprising determining the efficacy of the lesion created by the therapy probe based on the results of the imaging.

12. The method of claim 10, wherein the creating comprises applying the electrical current through the tissue.

13. The method of claim 10, wherein the creating comprises directing the ultrasonic energy to the tissue.

14. The method of claim 10, wherein the imaging comprises directing the ultrasonic energy through the tissue.

15. The method of claim 11, wherein the determining comprises performing normal B-scan ultrasonic imaging of the lesion.

16. The method of claim 11, wherein the determining comprises performing ultrasonic Doppler enhanced imaging of the lesion.

17. The method of claim 16, wherein the ultrasonic Doppler enhanced imaging of the lesion comprises sonoelastic imaging of the lesion.

18. The combination therapy and imaging instrument of claim 1, wherein the therapy and imaging probes being operatively connected to a common ultrasonic generator.

19. An instrument for imaging lesions in tissue, the instrument comprising:

an imaging probe for imaging the lesion using ultrasonic energy, the imaging probe comprising a side surface and connecting means formed on the side surface for releasable connection of a separable therapy probe for producing energy to create the lesion thereon, wherein the therapy probe includes a side surface adapted to appose the side surface of the imaging probe and an energy transmitting surface adapted to be in contact with the surface of the tissue and the imaging probe includes an ultrasonic energy transmitting surface adapted to be in contact with the surface of the tissue;

when the imaging probe and the therapy probe are releasable connected by the connecting means and the side surface of the therapy probe and the side surface of the imaging probe are apposed each other, the ultrasonic energy transmitting surface of the imaging probe and the energy transmitting surface of the therapy probe are aligned with each other, to define a continuous unitary energy transmitting surface adapted to be in contact with the surface of the tissue for performing simultaneous tissue alteration and tissue imaging; and the energy produced by the therapy probe is at least one of ultrasonic energy and an electrical current, and wherein the imaging probe and the therapy probe are adapted to permit simultaneous energy production and imaging of the lesion during lesion creation.

20. A therapy probe for producing energy to alter tissue, the therapy probe having connecting means for releasable connection of a separable imaging probe for imaging the tissue using ultrasonic energy, wherein the therapy probe includes a side surface an energy transmitting surface adapted to be in contact with the surface of the tissue, and the imaging probe includes a side surface adapted to appose the side surface of the therapy probe and an ultrasonic energy transmitting surface adapted to be in contact with the surface of the tissue;

when the imaging probe and the therapy probe are releasably connected by the connecting means and the side surface of the therapy probe and the side surface of the imaging probe are apposed each other, the ultrasonic energy transmitting surface of the imaging probe and the energy transmitting surface of the therapy probe are aligned with each other, thereby defining a continuous unitary energy transmitting surface adapted to be in contact with the surface of the tissue for performing simultaneous tissue alteration and tissue imaging; and the energy produced by the therapy probe is at least one of ultrasonic energy and an electrical current, and wherein the imaging probe and the therapy probe are adapted to permit simultaneous energy production and imaging of the tissue during tissue alteration.

21. A method for forming a lesion in tissue, the method comprising:

releasably connecting a therapy probe comprising a side surface and an energy transmitting surface adapted to be in contact with the surface of the tissue to an imaging probe comprising a side surface and an ultrasonic energy transmitting surface adapted to be in contact with the surface of the tissue;

apposing the side surface of the therapy probe and the side surface of the imaging probe and aligning the energy transmitting surface of the therapy probe and the ultrasonic energy transmitting surface of the imaging probe, to define a continuous unitary energy transmitting surface adapted to be in contact with the surface of the tissue for performing simultaneous tissue alteration and tissue imaging;

creating a lesion in the tissue with energy produced by a therapy probe, wherein the energy produced is at least one of ultrasonic energy and an electrical current;

imaging the lesion created with an imaging probe connected to the therapy probe, wherein the imaging probe and the therapy probe are adapted to permit simultaneous energy production and imaging of the lesion during lesion creation;

determining the efficacy of the lesion created by the therapy probe based on the results of the imaging step; and controlling the creating based on the results of the determining step.

22. The method of claim 21, wherein at least one of the determining and controlling steps are automatically performed.

* * * * *